Figure 1:
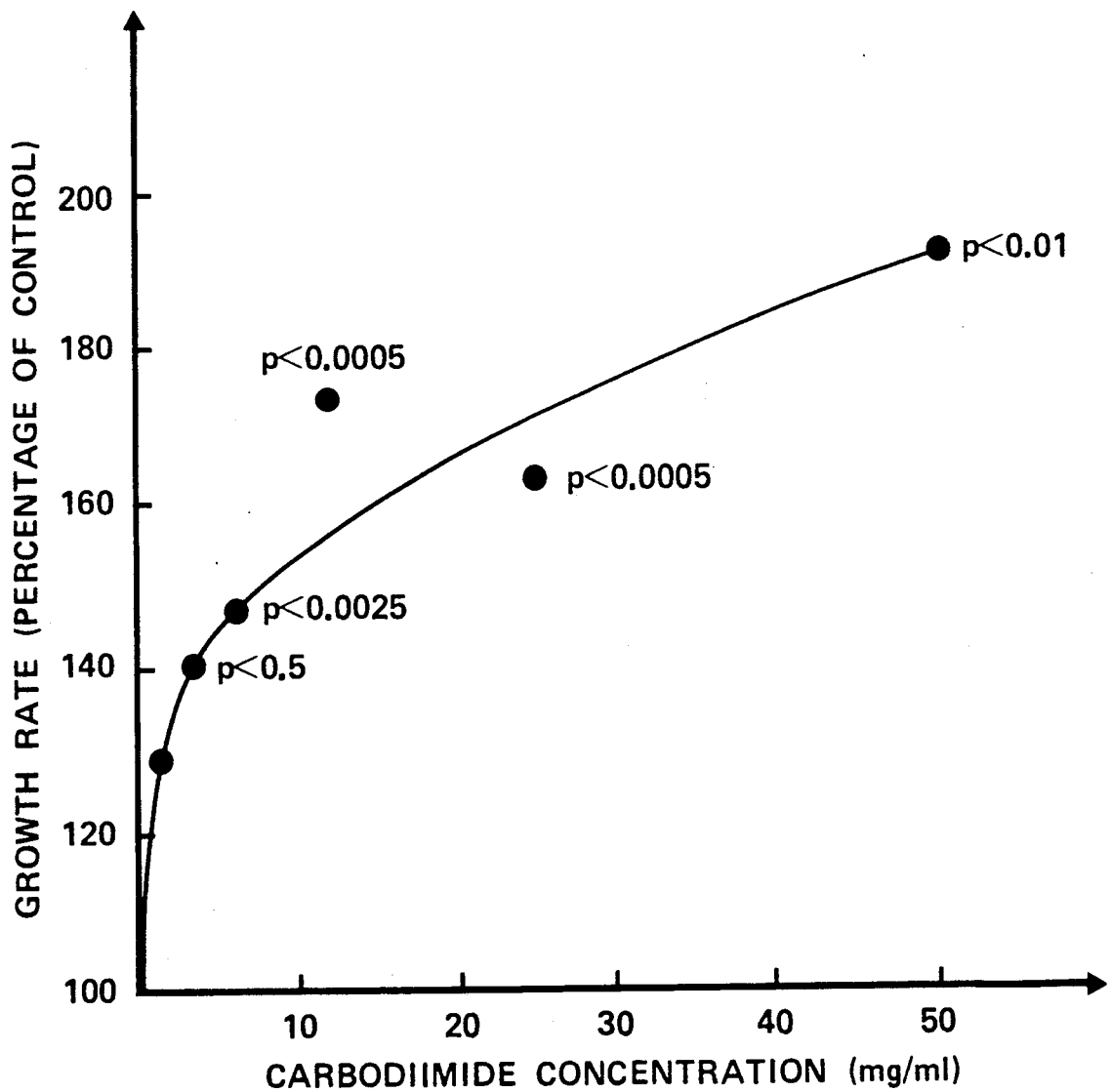

United States Patent [19] [11] Patent Number: 5,045,312
Aston et al. [45] Date of Patent: Sep. 3, 1991

[54] PHYSIOLOGICALLY ACTIVE COMPOSITIONS OF GROWTH HOMONE AND SERUM ALBUMIN OR IG G

[75] Inventors: Roger Aston; Robert Bomford, both of Beckenham; Andrew T. Holder, London, all of England

[73] Assignee: Burroughs Wellcome Co., Research Triangle Park, N.C.

[21] Appl. No.: 265,278

[22] Filed: Oct. 27, 1988

Related U.S. Application Data

[63] Continuation of Ser. No. 829,716, Feb. 14, 1986, abandoned.

[30] Foreign Application Priority Data

Feb. 18, 1985 [GB] United Kingdom ................ 8504099

[51] Int. Cl.$^5$ .................... A61K 37/36; A61K 39/44; A61K 39/395
[52] U.S. Cl. .................... 424/85.8; 514/12; 514/21; 530/363; 530/391
[58] Field of Search ............... 424/85.8; 530/363, 391; 514/21, 12

[56] References Cited

U.S. PATENT DOCUMENTS 3,645,852  2/1972  Axen et al. ............................ 195/68
4,003,792  1/1977  Mill et al. .............................. 195/63
4,302,386  11/1981  Stevens ................................ 530/399
4,464,468  8/1984  Avrameas et al. .................... 530/363

FOREIGN PATENT DOCUMENTS 119650  9/1984  European Pat. Off. .
2115281  2/1982  United Kingdom .

OTHER PUBLICATIONS

Atassi et al., *Biochimica et Biophysica Acta* 670 (1981) pp. 300–302.
Carlsson et al., *Biochem. J.* 173, 1978, pp. 723–737.
Topper et al., *Biochem. & Biophys. Res. Comm.*, 66(2): 793 (1975
Molteni et al., *Chem. Abstracts*, 83: 48130h (1975).
Vonderhaar et al., *Biochem. & Biophys. Res. Comm.*, 60(4): 1323 (1974).
Gestler et al., *Chem. Abstracts*, 102: 180588d (1985).
Mashita et al., *Chem. Abstracts*, 102: 40414n (1985).
Schepper et al., *Chem. Abstracts*, 101: 184415x (1984).
Cadwallader et al., *Chem. Abstracts*, 94: 180597X (1981).
Oka et al. (I), *Science*, 188: 1317 (1975).
Oka et al. (II), *Proc. Nat. Acad. Sci.*, 71(5): 1630 (1974).
Wilchek et al. *Proc. Nat. Acad. Sci.*, 72(3): 1055 (1975).
Dvorak et al., Ca vol. 89, 1978, #142819k.
Varner et al., Ca vol. 92, 1980, #161571b.
Fujii et al., Ca 103, 1985, #37724k.
Erba et al., Ca 89, 1978 #142889h.
Dovorak et al., *Radiochem. Radioanal. Letters* 34 (2–4) 155–160 (1978).

*Primary Examiner*—Howard E. Schain
*Assistant Examiner*—Choon P. Koh
*Attorney, Agent, or Firm*—Donald Brown

[57] ABSTRACT

Growth hormone is conjugated to any ligand, preferably a protein such as bovine serum albumin, optionally by use of a cross-linking agent such as a carbodiimide. The conjugates have enhanced activity when compared with unmodified growth hormone, and also better aqueous solubility at acid pH's.

9 Claims, 3 Drawing Sheets

PHYSIOLOGICALLY ACTIVE COMPOSITIONS OF GROWTH HOMONE AND SERUM ALBUMIN OR IG G

This is a continuation of co-pending application Ser. No. 06/829,716 filed on Feb. 14, 1986.

This invention relates to physiologically active substances.

Growth hormone (GH) is the major pituitary hormone and is largely responsible for causing growth in vertebrates and lactogenesis in mammals. It is a single polypeptide chain of about 191 amino acids. EP-A-119 650 (Procter and Gamble) discloses conjugates formed from insulin and smell molecules (for example disaccharides) having at least one D-galactosyl group. These conjugates have less activity (70-75%) than native insulin, but are specifically targeted to the liver, because insulin receptors on hepatocytes have a high affinity for D-galactosyl groups. Insulin metabolism is such that delivery of insulin to the liver in preference to other tissues is desirable. There is no suggestion that such conjungation would be desirable with other hormones and other ligands, not least because hormone-receptor binding is a highly specific interaction.

It has now been found that the activity of GH can be enhanced if the GH is covalently linked, i.e. conjugated, to a ligand. The term "ligand" is used in this specification to mean any molecule which may directly, or via a cross-linking agent, be linked covalently to GH.

Thus, one aspect of the present invention provides a compound comprising growth hormone (GH) conjugated to a ligand.

Each species of vertebrate has its own GH, although there is often extensive sequence homology between two different GH's and equally, GH from one species will sometimes cause growth in another species. Thus, enhancement of a given GH may be tested for in any species in which that GH causes growth. Similarly, GH can be modified by adding or deleting amino acids, or by replacing certain amino acids by others, without necessarily destroying the growth promoting activity of the GH. Thus, the terms "growth hormone" and "GH" in this specification include such GH variations and fragments, whether isolated from natural sources, chemically synthesised or genetically engineered.

A second aspect of the invention provides a pharmaceutical composition comprising a compound as above and a pharmaceutically acceptable carrier.

The invention also provides a method of causing or enhancing growth in a vertebrate by administration to that vertebrate of a compound as above.

Such a method may be employed to cause a dwarf child lacking in sufficient endogenous GH to grow more normally, or to cause economically important animals either to grow to a larger size or to attain their normal full size more rapidly.

The compounds of the invention may be made by using a suitable cross-linking agent.

The term "cross-linking agents" is used in this specification to mean those compounds with two reactive groups, at least one of which will react covalently with growth hormone and at least one of which will react covalently with a ligand. Suitable cross-linking agents include acid chlorides, mixed anhydrides glutaraldehyde, diazotising reagents (e.g. p-nitro-benzoyl chloride), carbodiimides (such as $N,N^1$-dicyclo-hexylcarbodiimide), acylimidazoles, bifunctional imidoesters (such as dimethyl adipidimate dihydrochloride), bifunctional NHS esters (such as N-hydroxy-succinimide esters, e.g. succinimidyl tartrate) and others, many of which are available from Pierce Chemical Company (Pierce and Warriner, Chester, U.K.). Cross-linking agents may react with amino, carboxyl or other groups on the GH and ligand. Conveniently, the cross-linking agent and/or ligand are so chosen that the ligand is bound to an amino group on the GH.

The amount of cross-linking agent which is used will depend upon the particular cross-linking agent, GH and ligand being used. In general, too little cross-linking agent may fail to produce the desired concentration of conjugates, whereas too much may produce large agglomerations of conjugates which are insoluble or otherwise ineffective. With a GH concentration of about 600 µg/ml, concentrations of cross-linking agent of about 5 to 300 mg/ml are preferred, more preferably about 10 to 150 mg/ml, most preferably about 30 to 125 mg/ml. The hormone and ligand will normally be mutually equimolar, although an excess of ligand may be employed to prevent wastage of GH resulting from the formation of GH-GH conjugates.

Thus, a further aspect of the invention provides a process for preparing a compound as above, by mixing GH with a ligand in the presence of a cross-linking agent.

It is possible, and sometimes desirable, for either the GH or the ligand first to be mixed with the cross-linking agent before the other component is added.

Preferably the ligand is a protein, particularly serum albumins or immunoglobulins (e.g. Ig G). Water-soluble ligands are preferred. Undesirable immunological reactions in the animal to which the compound of the invention is being administered may be largely or entirely avoided by using at the ligand a molecule of the animal in question. Thus, a suitable ligand when cows are being treated is bovine serum albumin, whereas porcine serum albumin may be used for pigs.

Instead of cross-linking agent and a relatively inert separate ligand, a more reactive ligand can be used which will react directly with the GH.

Preferably, the ligand has a molecular weight of between 100 and $10^6$ daltons, more preferably between 1000 and 500 000 dalts, most preferably between 10,000 and 250,000 daltons.

In selecting the site to which the ligand is to be bound, it is prima facie important not to block the site on the GH which interacts with the GH-receptors in the liver or elsewhere responsible for promoting growth. Thus, candidate conjugate compounds have been subjected to competition radioimmunoassay (RIA) studies (with unconjugated GH) as well as determination of binding to liver microsome preparations, to assess whether such a site is blocked, in order to avoid having to conduct a growth study on a vertebrate. Conversely, it may be desirable to block the site on the GH which binds to receptors in other tissues of the body. A corresponding competition RIA study using an NB2 lymphoma cell line (available from Dr. R. L. Noble, Cancer Control Agency of British Columbia, 2656 Heather Street, Vancouver, or Wellcome Res. Labs, Beckenham, Kent, UK.) may therefore be used to determine the extent to which such a site is blocked.

Conjugated compounds in accordance with the invention have been found to be more readily soluble than the corresponding unconjugated GH. The relative insolubility of bovine GH, particularly at PH's which are otherwise suitable for GH-containing formulations, has been regarded as a disadvantage when administration of GH to cattle has been contemplated.

Compositions in accordance with the invention may be in any suitable form. Parenteral administration is preferred, especially by use of slow-acting "depot" formulations. Carriers for such formulations may be porous (such as soluble glass), swellable (such as hydrogels) or thermoplastic (such as polyhydroxybutyric acid). In the first case, the pores of the carriers are filled with a solution of the conjugate, and excess solvent is then evaporated off to give a concentration of GH of about 0.01 to 25%, preferably 1 to 25%. Swellable polymers absorb a solution of the conjugate to give concentrations of about 0.01 to 50% GH, preferably 1 to 50%, whereas thermoplastic polymers are simply mixed with the conjugate and formed, by application of heat and/or pressure, into suitable shapes. Concentrations of about 0.01 to 50%, preferably 1 to 50%, may be reached in this way. Pellets, rods, blocks, films, strands and mesh sheets may be used. Alternatively, the compounds of the invention may be dispensed by an automatic or remotely-controlled pump implanted in the host animal's body, such as those pumps used for the administration of insulin to diabetics. Such compositions and pumps would normally be inserted subcutaneously into the host animal and remain there for some time. In humans, however, injections of suitable formulations may be preferred to such depot formulations.

The invention will now be illustrated by reference to the following non-limiting Examples.

EXAMPLE 1

Enhancement of human GH activity by conjugation to mouse immunoglobulin

Mice of the Snell-dwarf[1] strain, which are characterised by hypoplasia of the anterior region of the pituitary bland, were used at the age of 10-12 weeks (7-10 g) to compare the bioactivities of human growth hormone (hGH) either free or conjugated to immunoglobulin with carbodiimide. Male and female animals were randomised and allocated to cages so that no two mice of the same treatment group were in the same cage. Hormone or conjugate were administered subcutaneously (0.1 ml) on two consecutive days before injection of $Na_2{}^{35}SO_4$ (0.5 $\mu$Ci/g) (Amersham Radiochemicals, U.K.) for a further 24 hours. Growth rate was measured by the incorporation of radioactivity into costal cartilage which articulated directly with the sternum after removal of the soft tissue and solubilization in formic acid. The means growth of each treatment group ($\pm$SEM) was expressed as dpm/mg of cartilage and represents the uptakes of $^{35}SO_4{}^{2-}$ from groups of six animals. Statistical significance was determined by the unpaired Student T-test.

Human growth hormone was purified from clinical grade material which was outdated or otherwise not suitable for human use. MRC therapeutic grade hGH purified to an activity of 2 I.U./mg (gift from Dept. of Health and Social Security (DHSS), London) was chromatographed on Sepnadex G-78 or by SDS-polyacrylamide gel electrophoresis under reducing conditions to yield a single band corresponding to $M_r$ 22 000.

To obtain the conjugates, equimolar concentrations of hGH and immunoglobulin (1 mg/ml and 8.0 mg/ml final respectively) were incubated at 22° C. (2 hrs) in the presence or absence of varying concentrations of carbodiimide (0-50 mg/ml) in phosphate buffered saline (PBS) pH 7.2. Carbodiimide [1-ethyl-3-(3-dimethylaminopropyl)carbodiimide HCl] is obtainable from Pierce or Biorad. The resulting material was dialysed extensively against BPS, centrifuged and assessed for bioactivity in vivo. Growth rate by conjugated hormone was increased in a dose-dependent fashion in relation to the concentration of carbodiimide. Maximum enhancement was observed with carbodiimide at 50 mg/ml and corresponded to a 1.9 x increase in growth rate. The results are given in FIG. 1.

EXAMPLE 2

Enhancement of bGH activity in vivo by conjugating hormone to BSA

Bovine growth hormone (bGH) (purified from bovine pituitaries as described in (Hart et al, 1984, Biochem, J., 218, 573) was conjugated to globulin-free BSA obtainable from (Sigma) at equimolar concentrations (1 mg/ml and 3.75 mg/ml respectively) in the presence of carbodiimide (50 mg/ml). Incubations and measurement of bioactivity were performed as described for Example 1. From the results given in Table 1, it can be seen that growth rate was enhanced more than two-fold by the conjugated hormone in comparison with mixtures of unconjugated bGH and BSA (significance $P<0.0005$).

TABLE 1

| Components of Conjugate | Growth Rate (dpm/mg of costal cartilage) |
| --- | --- |
| bGH + BSA (ie. unconjugated) | 530 ± 50 |
| bGH + BSA + carbodiimide | 1250 ± 100 |

EXAMPLE 3

Enhancement of hGH activity by conjugation to BSA with glutaraldehyde

Equimolar concentrations of hormone and albumin (1 mg/ml and 3.75 mg/ml respectively) were incubated in the presence of glutaraldyude (0.0125%-1.25% v/v) at 22° C. for 2 hours prior to extensive dialyses against PBS to remove the conjugating agent. The relative potency of the conjugates was measured as described above, and the results are given in Table 2. Significant enhancement ($p<0.01$) was observed at one dose of glutaraldehyde (0.125%, v/v).

TABLE 2

| Compounds of Conjugate | | | Growth Rate (dpm/mg of | |
| --- | --- | --- | --- | --- |
| hGH | BSA | glutaraldehyde | costal cartilage) | Significance |
| / | / | — | 235 ± 35 | (Control) |
| / | / | 1.25% (v/v) | 296 ± 14 | N.S. |
| / | / | 0.125% | 388 ± 33 | p < 0.01 |
| / | / | 0.0125% | 170 ± 42 | N.S. |
| / | — | 1.25% | 160 ± 52 | (Control) |

N.S. means that the difference was not significant.

EXAMPLE 4

Enhancement of hGH activity by conjugation to different ligands with carbodiimide Human growth hormone was conjugated to BSA or murine immunoglobulin at equimolar concentrations of hormone and ligand and at a carbodiimide concentration of 50 mg/ml. Growth rate was monitored in dwarf mice as described above. As can be seen in Table 3, significant enhancement of growth rate was observed in conjugates with BSA and immunoglobulin. Groups treated with hormone only grew 30% as well as animals receiving the corresponding conjugates.

| Growth Promoter | Growth Rate (dpm/mg of costal cartilage) | Significance |
|---|---|---|
| hGH alone | 890 ± 70 | control |
| hGH + BSA | 1400 ± 270 | control |
| hGH + BSA + Carbodiimide | 2800 ± 260 | p < 0.025 |
| BSA + saline | 200 ± 30 | control |
| hGH + I g G + Carbodiimide | 2680 ± 450 | <0.0125 |

EXAMPLE 5

Increased solubility of bGH at low pH following conjugation to BSA

Figure 2:
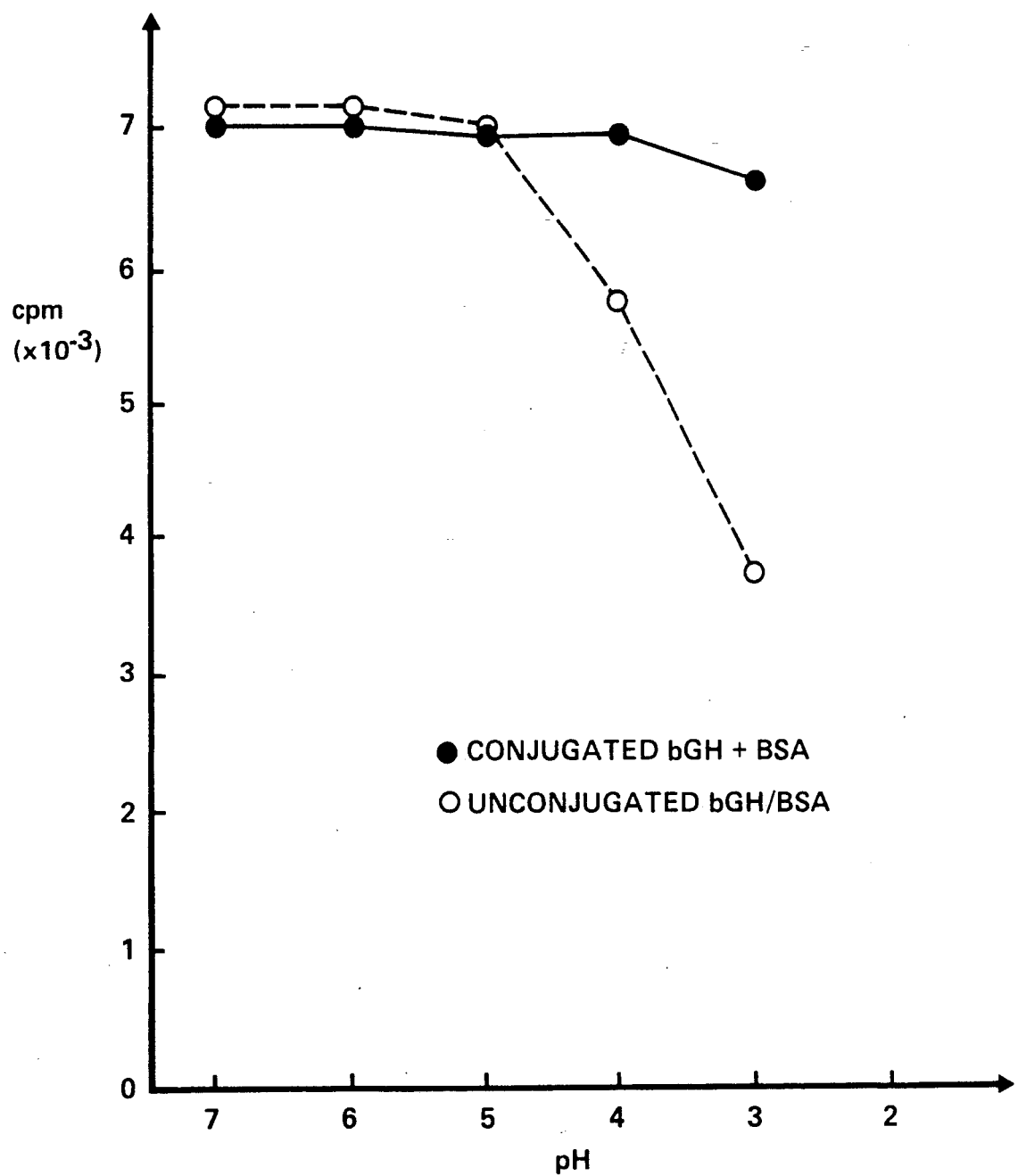

Bovine growth hormone was conjugated to BSA at equimolar concentrations (1 mg/ml and 3.75 mg/ml final respectively) in the presence of carbodiimide (50 mg/ml) at pH 7.2 for 2 hours at 22° C., prior to extensive dialyses against PBS to remove excess conjugating agent. Control material was treated identically in the absence of carbodiimide (i.e. equimolar bGH and BSA only) and solubility was determined by measuring the quantity of radioactivity ($^{125}$I-bGH included as tracer) precipitated after centrifugation at 30,000 g. All steps following cross-linking were performed at 22° C. The pH of the corresponding samples was reduced by addition of 0.5 M sodium phosphate buffer at the pH values indicated in FIG. 2.

EXAMPLE 6

Competition RIA studies[2,3] conducted with the gGH-BSA conjugate described above or unconjugated hGH/BSA against four monoclonal antibodies to hGH showed that the potentiating conjugate preferentially blocked the site (epitope) bound by EBO1.

TABLE 4

| Relative epitope potency of hGH-BSA conjugate (ie. ratio of conjugate to unconjugated hGH/BSA control) | |
|---|---|
| Monoclonal Antibody | Potency |
| EB01 | 57.0 |
| EB02 | 6.4 |
| NA71 | 16.0 |
| QA68 | 12.4 |

EXAMPLE 7

Enhancement of human GH activity after conjugate to BSA

Following the general method of Example 1, but using 550 μg/ml of hGH, 3.4 mg/ml of BSA and a varying proportion of disuccinimidyl tartrate (DST), conjugates of hGH and BSA were prepared. Using the same activity assay as in Example 1, the results given in Table 5 were obtained.

TABLE 5

| Concentration of DST log$_{10}$ (mg/ml) | Growth (dpm/mg) |
|---|---|
| none | 1450 ± 101 |
| −1 | 1800 ± 290 |
| 0 | 2351 ± 224 |
| 1 | 2209 ± 160 |

TABLE 5-continued

| Concentration of DST log$_{10}$ (mg/ml) | Growth (dpm/mg) |
|---|---|
| 2 | 2960 ± 339 |

EXAMPLE 8

Effect of Conjugation of hGH to BSA or poly(Glu)

Using the method of Example 1, hGH (580 μg/ml) conjugated to BSA (3.6 mg/ml) or polyglutamic acid (580 μg/ml) of either 11,000, 32,000 or 60,000 molecular weight (available from Sigma, Poole, Dorset, UK), the cross-linking agent being carbodimide ( ). The results, given in Table 6, show a slight increase in enhancement as the MW of the poly(glu) increases.

TABLE 6

| Ligand | Growth (dpm/mg) |
|---|---|
| none | 3500 ± 500 |
| BSA | 8200 ± 400 |
| 11K poly (glu) | 7850 ± 550 |
| 32K poly (glu) | 8100 ± 250 |
| 60K poly (glu) | 8600 ± 350 |

EXAMPLE 9

Effect of differing concentrations of cross-linking agent

Figure 3:
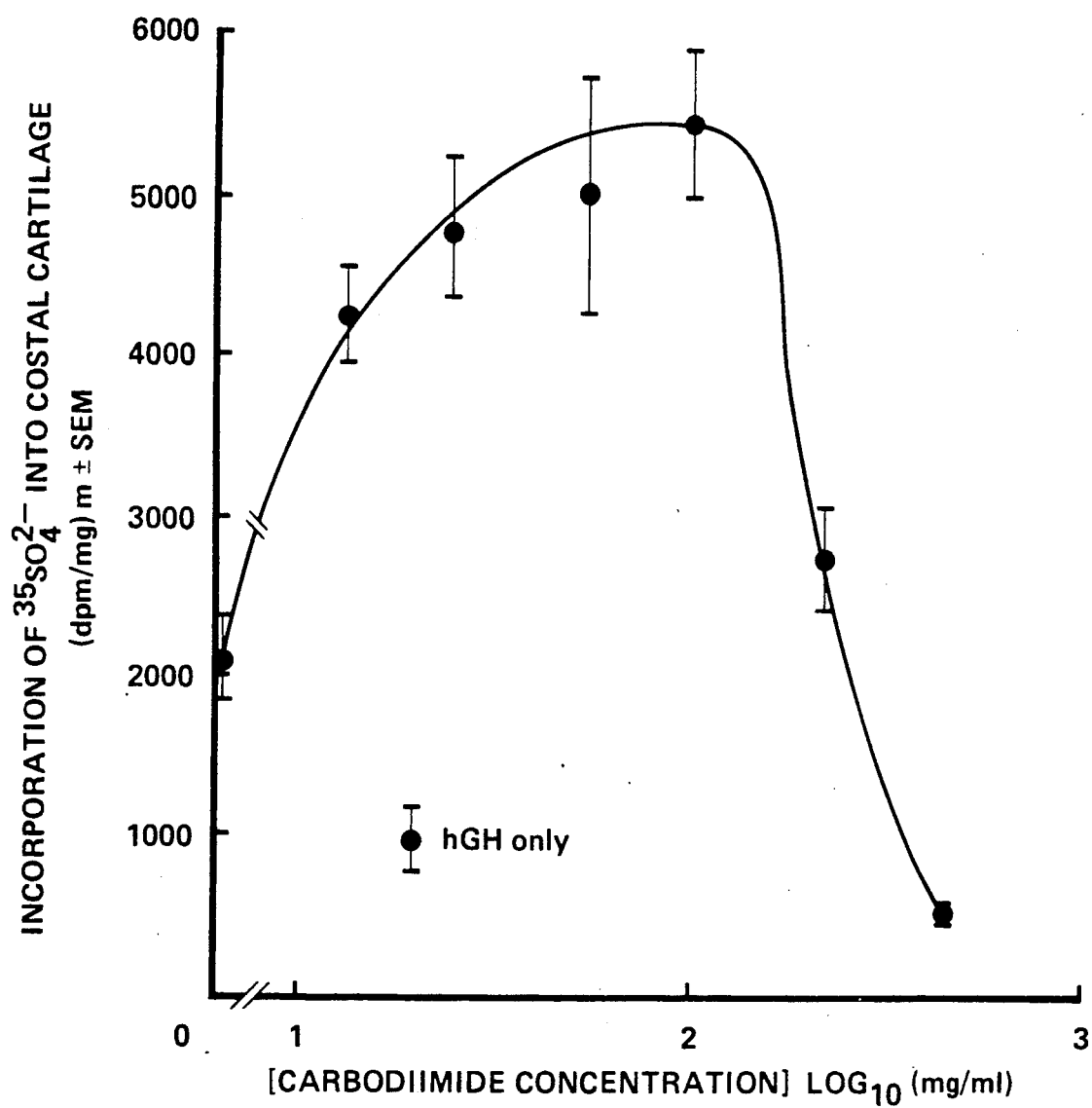

Using the method of Example 1 (but incubating for 4 hours), hGH (600 μg/ml) was conjugated to BSA (3.6 mg/ml) in the presence of differing concentrations of carbodimide (CAD). The results, shown graphically in FIG. 3, show that CAD concentrations of about 7–200 mg/ml (log$_{10}$ (mg/ml) of about 0.88 to 2.34) produce enhancing conjugates, with maximum activity being reached at about 30 to 125 mg/ml.

EXAMPLE 10

Effect of different ligands on enhancement of HGH activity

In a similar experiment of that of Example 4, hGH (600 μg/ml) and differing ligands (1:2 hGH:ligand molar ratio) were conjugated by carbodimide (CAD) (40 mg/ml) in a 2 hour incubation at pH 7.2 PBS. The results of the growth assay of Example 1 are given in Table 7.

TABLE 7

| Conjugate or Control | Growth (dpm/mg) |
|---|---|
| Saline | 200 ± 50 |
| hGH + BSA (no CAD) | 1375 ± 210 |
| hGH + BSA + CAD | 2800 ± 275 |
| hGH + lysozyme + CAD | 1900 ± 150 |
| hGH + I g G. + CAD | 2875 ± 175 |
| hGH + Ac-BSA + CAD | 2775 ± 200 |

REFERENCES

1. Holder, A. T., Wallis, M, Biggs, P. and Preece. M. A. J. Endorinol. 85:35-47 (1980).
2. Ivanyl, J. Molec. Immunnol. 19 1611-1611(1982).
3. Aston, R, Cooper, L, Holder, A., Ivanyi. J. and Preece, M. A. Molec. Immunol. (IN PRESS) (1985).

Formulation Examples

1. Soluble glass

Soluble phosphate glass is sintered and an aqueous solution of a BSA-GH conjugate applied thereto and allowed to dry, to give a final concentration of 20% conjugate.

2. Polyhydroxybutyric acid

Polyhydroxy butyric acid is mixed with a BSA-GH conjugate and compression moulded into 1g pellets continuing 30% GH.

3. Polyactide formulation

The techniques described in EP 58 481 (ICI) are used to produce implantable pellets having 10-50% GH-mouse 1 gG.

What is claimed:

1. A method of increasing growth hormone regulated response in a vertebrate which comprises administering to said vertibrate, a composition comprising an effective growth causing or enhancing an amount of non-immunogenic pharmaceutically acceptable, growth stimulating conjugated compound of growth hormone linked to a ligand which is selected from serum albumin or immunoglobulin.

2. The method of claim 1, in which the ligand is bovine serum albumin.

3. The method of claim 2, in which the vertebrate is a dwarf child.

4. A method of increasing growth hormone regulated response in a vertebrate which comprises administering to said vertibrate a composition comprising an effective growth causing or enhancing an amount of a non-immunogenic pharmaceutically growth stimulating conjugated compound of growth hormone linked to a ligand which is selected from serum albumin or immunoglobulin, and wherein said growth hormone is linked to said ligand by a cross linking agent.

5. The method of claim 4 in which said cross linking agent is carbodiimide, glutaraldehyde, acid chloride, mixed anhidride, acylimidazale, or N-hydroxy succimmide ester.

6. The method of claim 4 in which the cross-linking agent or ligand binds to an amine group of the growth hormone.

7. The method of claim 4 in which the cross linking agent is glutaraldehyde.

8. The method of claim 4 in which the cross linking agent is carbodiimide.

9. A method of increasing growth hormone regulated response in a dwarf child, which comprises administering to said dwarf child, a composition comprising an effective growth causing or enhancing amount of non-immunogenic pharmaceutically acceptable, growth stimulating conjugated compound of growth hormone linked to a ligand which is selected from serum albumin or immunoglobulin.

* * * * *